United States Patent [19]
Enk

[11] Patent Number: 6,086,559
[45] Date of Patent: *Jul. 11, 2000

[54] METHOD AND DEVICE FOR PRESSURE-CONTROLLED HANDLING OF A FLUID, IN PARTICULAR FOR MEDICAL PURPOSES

[76] Inventor: Dietmar Enk, Ludgerusstrasse 2, D-48653 Coesfeld, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/894,104

[22] PCT Filed: Jan. 31, 1996

[86] PCT No.: PCT/EP96/00402

§ 371 Date: Oct. 10, 1997

§ 102(e) Date: Oct. 10, 1997

[87] PCT Pub. No.: WO96/23539

PCT Pub. Date: Aug. 8, 1996

[30] Foreign Application Priority Data

Feb. 2, 1995 [DE] Germany .................. 195 03 230

[51] Int. Cl.[7] ............................................ A61M 1/00
[52] U.S. Cl. ...................... 604/121; 604/190; 604/236
[58] Field of Search .................... 604/119, 121, 604/190, 191, 204, 207, 236, 31; 600/578, 579

[56] References Cited

U.S. PATENT DOCUMENTS 4,624,659 11/1986 Goldberg et al. .................. 604/121
4,660,569 4/1987 Etherington .................. 604/190 X

*Primary Examiner*—Wynn Wood Coggins
*Assistant Examiner*—A. T. Nguyen
*Attorney, Agent, or Firm*—Frohwitter; William Beard; Catherine L. Bell

[57] ABSTRACT

A process and a device for pressure controlled manipulation of a fluid (4a), in particular for medicinal applications. The device comprises a receptacle (1a) of variable volume to contain the fluid (4a), a pressure creation device (2a) for producing pressure on the fluid (4a), an opening (1c) for admitting and/or discharging to fluid (4a), a measuring channel (2e) of prescribed cross-section connected to the receptacle (1a), and a buffer (2d) of prescribed volume which communicates with the measuring channel (2e), the measuring channel (2e) and the buffer (2d) being filled with a compressible medium. The pressure creation device is preferably a piston (2a) which can be pushed into the receptacle (1a), the piston being sealed to the inner wall of the receptacle (1a) by a sealing means (2c). According to the invention, in particular medicinal syringes are improved in that a fluid (4a) can be injected with particular evenness and at a pressure which can be precisely controlled, for example into a cavity (10), or a body (9). The pressure is read or measured by determining the position of the boundary layer (8) between the fluid (4a) and the compressible medium in the measuring channel (2e), e.g. by means of a scale (2k). The size of the buffer (2d) in relation to the internal diameter of the measuring channel (2e) determines the precision of measurement and the damping properties at the time of injection.

39 Claims, 6 Drawing Sheets

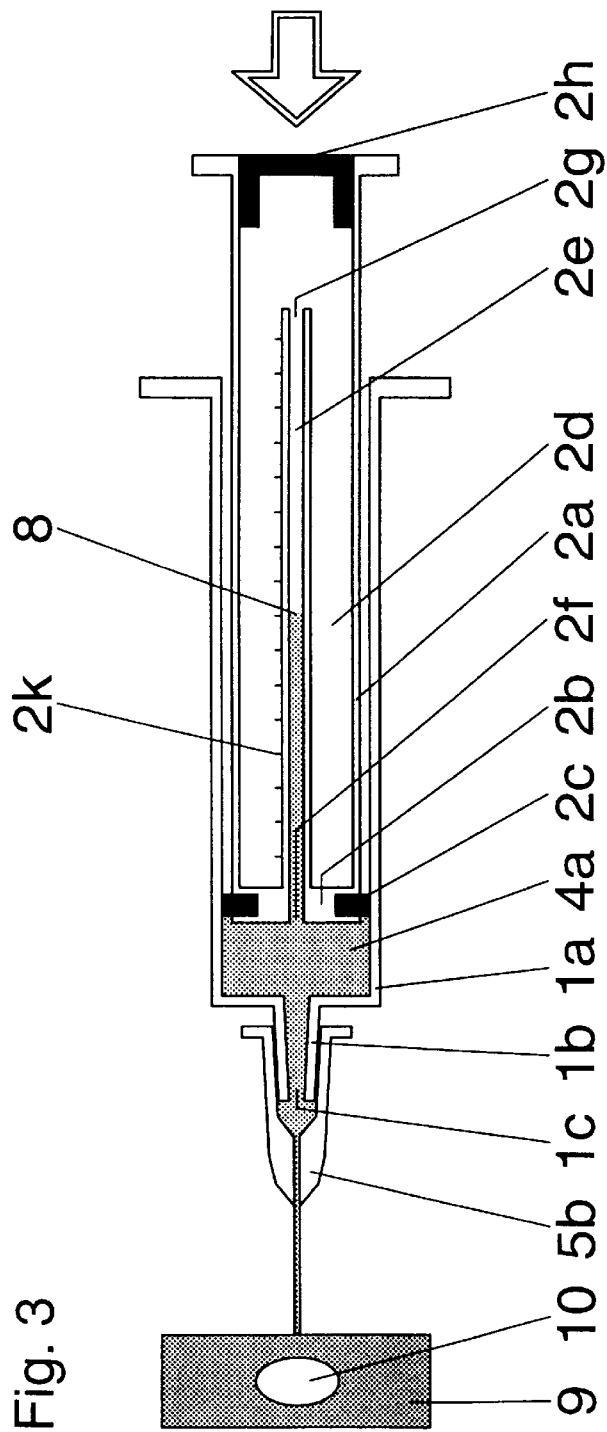
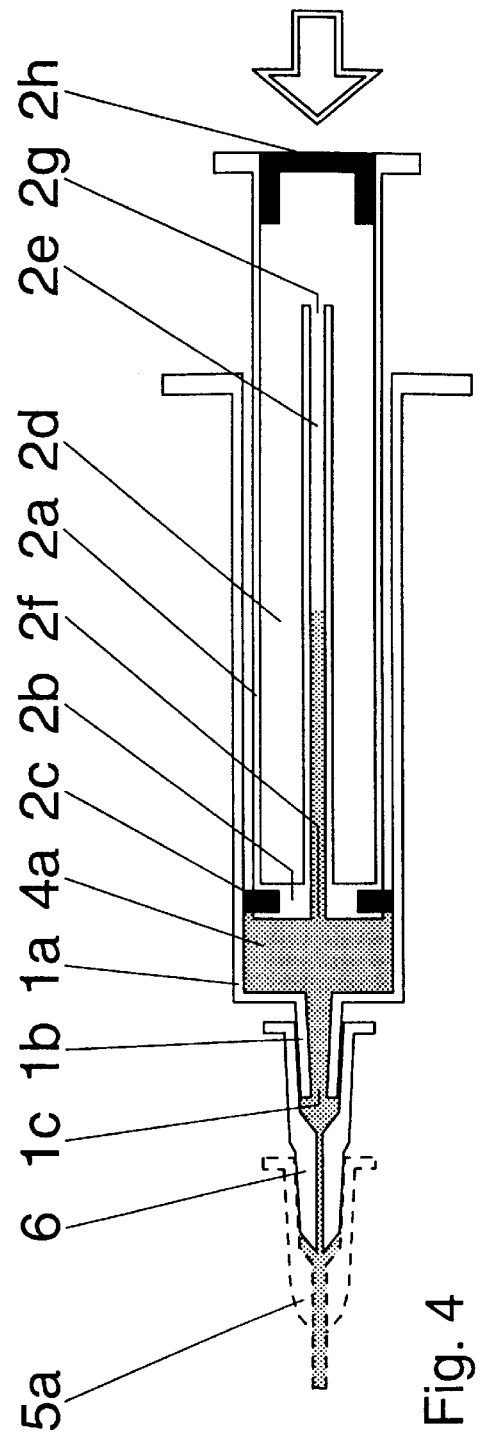

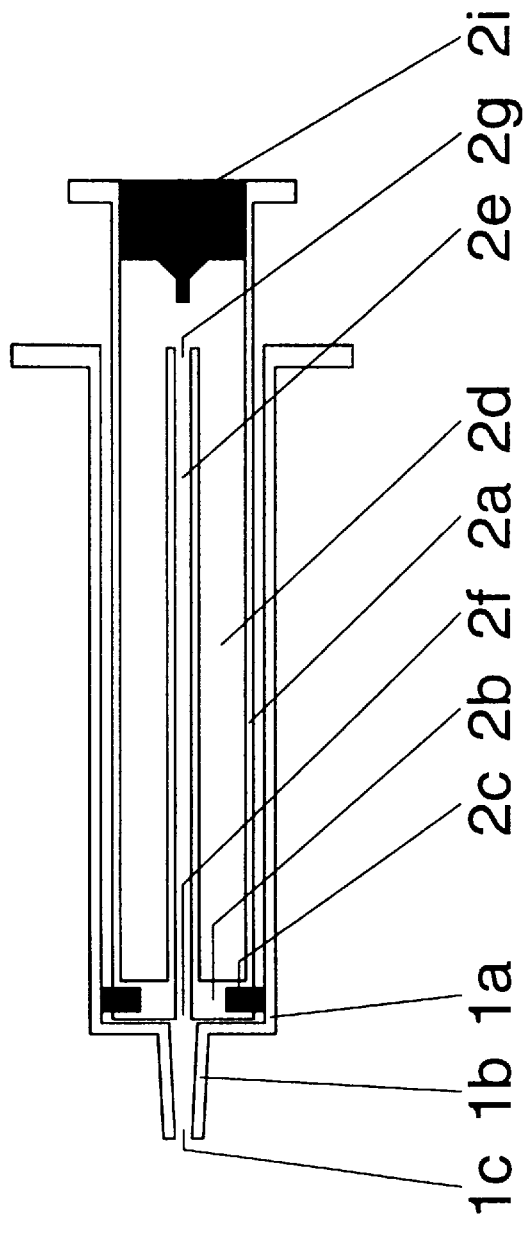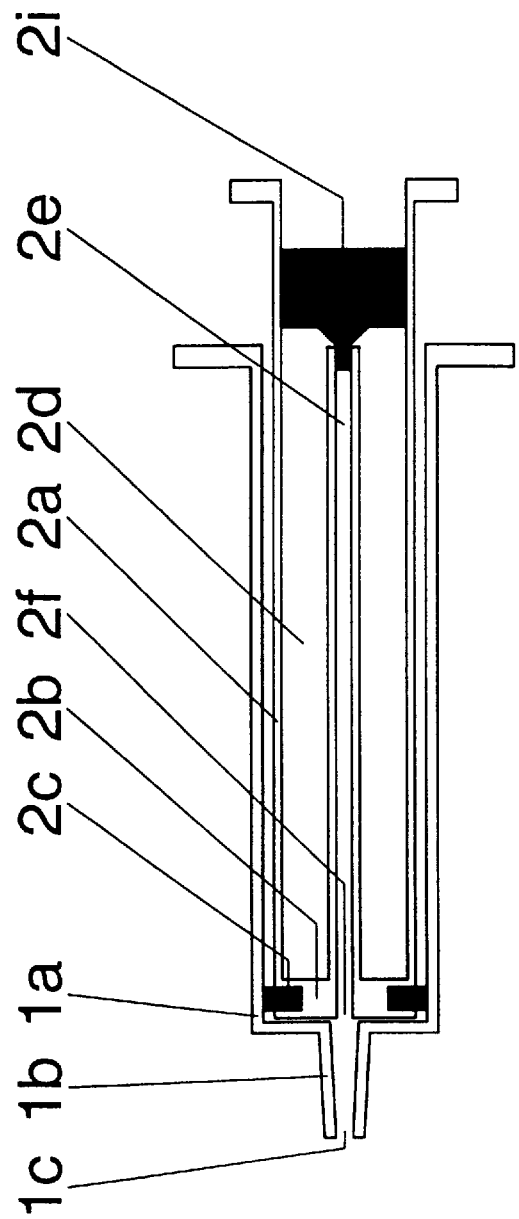

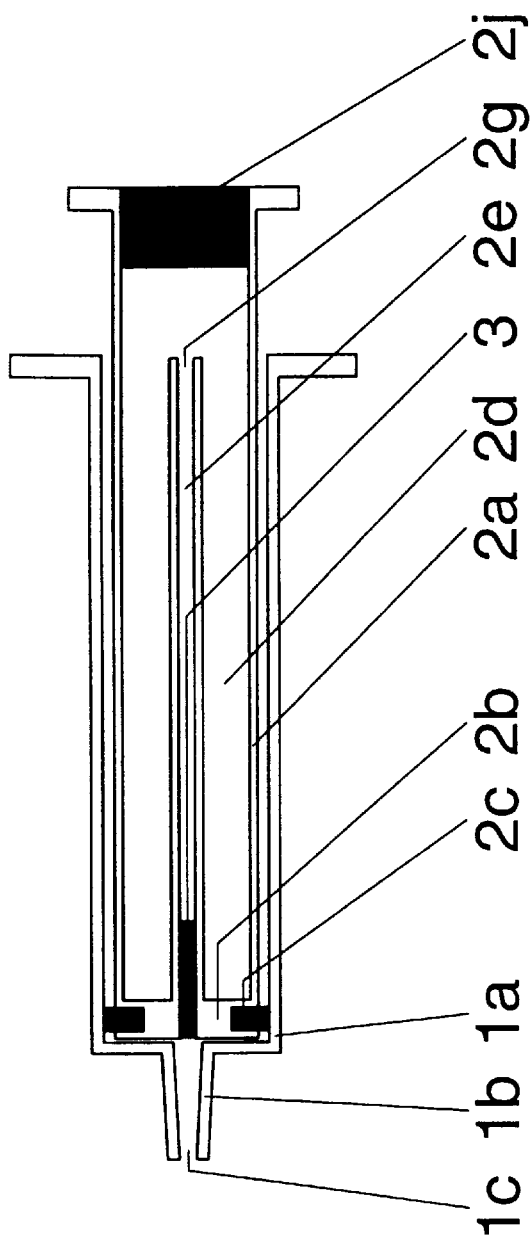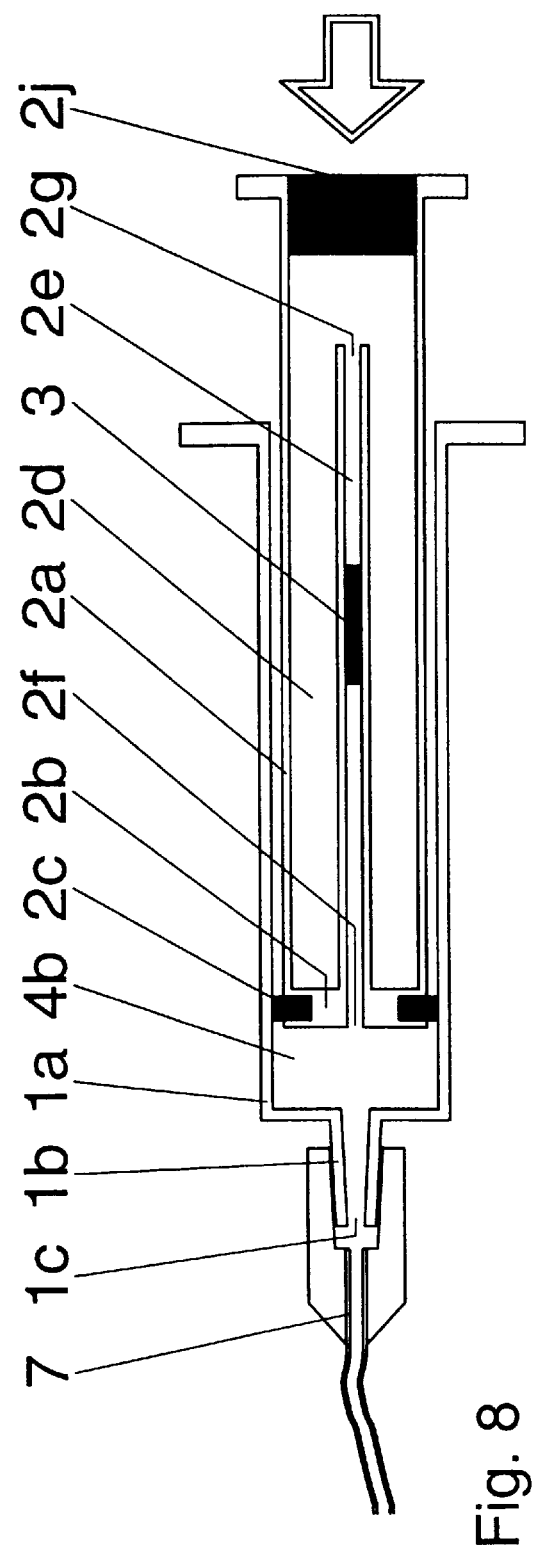

METHOD AND DEVICE FOR PRESSURE-CONTROLLED HANDLING OF A FLUID, IN PARTICULAR FOR MEDICAL PURPOSES

BACKGROUND OF THE INVENTION

The invention relates to a method and a device for pressure-controllable handling of a fluid. The device makes possible, in particular, even and steadied, in particular pressure-controlled, injection of a fluid, which can be a liquid or a gas. The device can also be used in different ways as a probe for inserting cannulas and when placing catheters. In particular, the invention relates to the further development of a syringe for medical purposes. A preferred field of application is anaesthesia.

SUMMARY OF THE INVENTION

Known devices for handling a fluid, in particular syringes, are provided with a container for receipt and delivery of a fluid, with a plunger which can be pushed into the container, sealed with respect to the internal wall of the container by sealing means. They are used mostly where a fluid is stored for a certain time before being used. Apart from medical applications, this can be a device for lubricating components, or also a device for precise pressure-controlled dosage of a fluid. In the case of such applications, in addition to the amount to be dosed, the pressure of the fluid when injected, the change in its pressure, or the speed of the fluid injection are of importance. These parameters must often be adjusted and monitored in order, for example, to prevent damage when the fluid is injected.

The operation and the use of a known device will hereinafter be described with reference to a syringe, using the example of spinal anaesthesia.

A usually suddenly occurring drop in blood pressure, with reflex tachycardia—due to expansion of blood vessels as a result of the blockade of pre-ganglion sympathetic nerve fibres (=sympatholytic action) often observed during spinal anaesthesia is an undesirable and occasionally dangerous complication in this anaesthetic procedure. All anaesthetists would therefore like to see spinal anaesthesia which is more controllable and the distribution of which can be better calculated, and the improved circulatory stability which can be obtained in this way particularly with patients with cardiac and circulatory diseases.

The sole use of so-called hyperbaric local anaesthetics, which are made heavier than the fluid by the addition of glucose, and are consequently preferably distributed in the deeper regions in contrast to isobaric local anaesthesia, does not lead—as was expected—to better control of a spinal anaesthesia in clinical practice.

Some in-vitro tests have shown that the current standard injection techniques using thin spinal needles cause significant eddying of the local anaesthetic in the fluid space, resulting in complete or at least widespread mixing, even of hyperbaric local anaesthesia, with the fluid. These injection techniques are not suitable for underlying the fluid with a hyperbaric local anaesthetic with little, or without eddying and to thus provide a necessary precondition for effecting the distribution of the anaesthetic by suitable manoeuvring of the patient's position. The injection stream resulting from the high speeds of injection can, moreover, result in neural irritation or even trauma.

In particular, a slow and even injection using a thin spinal needle, with which a turbulent injection stream occurs more rapidly at the same speed of injection compared to thicker needles, can prevent eddying of the local anaesthetic in the fluid and possible neural irritation or trauma by the injection stream. When using thin spinal needles such a slow and even injection is not possible manually with a conventional syringe, as minimal changes in pressure on the syringe plunger (=changes in the pressure effected by the fingers) results in unevenness in the injection stream, which causes eddies of the local anaesthetic in the fluid.

It is known that with a slow injection a certain steadying of the injection speed can be obtained by pneumatic dampening. For this, in addition to the local anaesthetic, several milliliters of air are drawn up into the syringe; by means of a three-way tap (90 degree offset) the syringe is placed perpendicularly on the spinal needle so that during the injection the air is located between the local anaesthetic and the plunger. The plunger is subsequently always pushed in just far enough for a slow reduction in the level of the local anaesthetic to be observed in the syringe.

Because of a distance measuring only a few millimeters between the nerve fibres on the left and the nerve fibres on the right-hand half of the body, a "true", that is to say motor, sensory and vegetative (in particular sympathetic) one-sided spinal anaesthesia is the clinical application for which the effectiveness of a certain technique or certain devices and aids can be examined with respect to the control and calculation of a spinal anaesthesia obtainable therewith. A method which makes it possible to apply a "true" one-sided spinal anaesthesia is also suitable for increasing the control, and consequently the safety of conventional, two-sided spinal anaesthesia.

Our own clinical study shows that by means of a pneumatically dampened, slow and even injection as described above (approximately 0.5 ml/min) of a hyperbaric local anaesthetic, using a thin spinal needle with a lateral outlet aperture (27 G Whiteacre) in the case of patient lying on his or her side, absolute or at least largely one-sided motor and sensory blockades are possible, in addition undesired sympatholytic effects on the side not numbed are minimised or can even be completely avoided, and the level of the spinal anaesthesia produced by positioning the patient is more controllable than previously.

The time needed for such an injection is greater but with shorter initiation times for producing the sensory and motor blockade, time is gained overall. The previous results make it conceivable that by targeted application of the local anaesthetic in the fluid space, the amount of local anaesthetic required can be reduced (smaller volume or lower concentration). This injection technique also appears to allow a more reliable underlying of the fluid with the local anaesthetic when a lower concentration glucose mixture is used than was previously usual with hyperbaric local anaesthetics, so use of a hyperbaric but iso-osmolar local anaesthetic is possible. Undesired hyper-osmolarity effects on the nerve fibres are in this way excluded.

The makeshift solution described for a pneumatically dampened injection proved appropriate, but necessitated unergonomic, difficult working with an unwieldy construction of a spinal needle, three-way tap and syringe. A device, in particular a syringe, is therefore desirable which can be handled ergonomically and in a normal manner and makes possible a slow and even or steadied injection of the local anaesthetic with reliable control of the injection pressure.

Syringes currently available with rubber or spring elements inserted or fitted in or on the plunger (DE 27 14 818 A1, DE 32 00 651 A1) allow the injection pressure to be more or less precisely indicated, but produce only very limited intentional steadying of the injection pressure, in particular of small pressure changes acting briefly upon the plunger, for example in spinal anaesthesia. The sometimes complex construction of such syringes and necessarily precise and thus expensive manufacturing almost excludes the use of such syringes as sterile single use items—such as are the currently required hygiene standard for certain applications, for example spinal anaesthesia.

A syringe with pneumatic plunger dampening (see unpublished German application P 44 28 467.5) provides, as shown by our own in-vitro experiments, steadying of the injection pressure and allows slow and even injections of a fluid (for example local anaesthetic) to be made freehand. By means of two plungers connected one behind the other in the syringe barrel, completely separated from one another by air, the pressure exerted by the fingers on the rear plunger (=compression plunger) always acts in a dampened manner upon on the front plunger (=injection plunger), by means of the compressed air located between the plungers. By altering the volume of the air located between the plungers and using the length of the front plunger as an indirect measurement of the maximum compression permissible and to be maintained—while avoiding direct contact between the two plungers—the desired injection speed can be adjusted and maintained. The precise functioning of this syringe requires a syringe barrel exactly the same size as the complete displacement path of the plunger, and for a certain injection speed a certain volume of air between the plungers. These relatively advanced production requirements generate a considerably higher price for such a syringe with pneumatic plunger dampening than for mass-produced low-cost single use syringes.

The currently available solution to the problem of a slow and even injection is an injection pump with precise operation even with low delivery rates. Such pumps are also technically very complex, therefore expensive to produce and service and—with respect to the situation during spinal anaesthesia—are too difficult and too time consuming to handle.

The object of the invention is to provide a method and a device with which a fluid can be handled in a pressure controllable manner, in particular during injections and other medical procedures on the human body.

The invention provides a method for pressure-controllable handling of a fluid, wherein the fluid located in a container of variable volume is made available by pressure at an outlet by means of said pressure acting upon the fluid, the container is connected to a measuring channel with a pre-determined cross-section, the measuring channel communicates with a buffer with a pre-determined volume, the measuring channel and the buffer are filled with a compressible medium, such that there is at least partial ingress of the fluid into the measuring channel, dependent upon the influence of the pressure, the cross-section of the measuring channel and the size of the buffer volume.

Accordingly, a device is also provided for pressure-controllable handling of a fluid, with a container of variable volume for receiving the fluid, a pressure producing means for producing a pressure acting upon the fluid, an outlet for the entrance and/or exit of the fluid, a measuring channel with a pre-determined cross-section, which is connected to the container, a buffer with a pre-determined volume, which communicates with the measuring channel, wherein the measuring channel and the buffer are filled with a compressible medium.

The invention will be described hereinafter with reference to the mode of operation of a syringe according to the invention and different methods for working with this syringe. The invention is, however, not limited to these preferred embodiments and the areas of application shown, but instead can be used for other comparable, in particular also non-medical, areas having the same or similar problems.

The device is a syringe for spinal anaesthesia, with which, without needing additional technology or staff, a local anaesthetic can be slowly and evenly manually injected into the spinal fluid, in particular by means of thin spinal needles, in order to avoid eddying of the local anaesthetic with the resultant undesired and unpredictable distribution of the spinal anaesthetic and traumatising of nerve fibres by the injection stream. The syringe is simple in production technology terms, and can also be manufactured cheaply with sufficient precision by mass-production.

In an advantageous embodiment, the syringe is provided with a dampening and pressure measuring means, which comprises a buffer (a hollow space filled with a compressible medium), of fixed or variable volume, located in the plunger of the syringe, and a measuring channel located in the side of the plunger located in the syringe barrel, leading into this buffer, lying centrically or eccentrically in the buffer and open at both sides. The buffer and the measuring channel are filled with a compressible medium, in particular air at atmospheric pressure.

By pulling back the plunger the container formed by the outer wall of the syringe and the base of the plunger is expanded and a low pressure is created in the syringe barrel, by means of which a liquid, for example a local anaesthetic, can be drawn up into the syringe barrel just as quickly as with a conventional syringe.

When the, for example vertically held, syringe is vented, the liquid now drawn up into the syringe barrel seals the front aperture, facing the liquid, of the measuring channel leading into the buffer of the plunger. This aperture of the measuring channel cannot exceed a certain diameter, depending on the viscosity of the liquid, as when venting the syringe the liquid can otherwise run into the measuring channel. With a front aperture with not too large a diameter of, for example, no more than 1 to 3 $mm^2$, the surface tension of the liquid is sufficient for the sealing. Additional separating means, for example an elastic stopper or a drop of oil, are used with injection of a gas in accordance with an advantageous further development of the syringe. The separating means should be selected such that the dampening effect and the precision of the pressure measurement change little. They should be easy enough to push into the measuring channel that their friction, compared to the normally occurring forces, is negligible.

By locking in the air located in the measuring channel and buffer of the plunger, with this syringe there is both a dampening element and a pressure measuring means in the plunger.

Now, if when pushing the plunger into the syringe barrel, that is to say when the container is reduced in size, the pressure with which the liquid is injected through a small lumen cannula with a relatively high flow resistance is exceeded by a certain amount, the liquid is partially pressed into the measuring channel—due to the comparatively low flow resistance herein. In this way displacement of the air located in the measuring channel occurs, and consequently compression of the air located in the measuring channel and buffer. If this pressure, by means of which a certain degree of air compression has been obtained, is subsequently exceeded, the liquid which has ingressed into the measuring channel is pressed out of the measuring channel again by decompression of the compressed air in the measuring channel and buffer.

On the one hand, such sudden changes in pressure acting upon the plunger and consequently on the liquid—such as cannot be avoided during a manual injection when the plunger is pushed too quickly into the syringe barrel—are effectively dampened. In addition by means of the direct, frictional contact of the liquid with the air, as a dampening, yet compressible medium, a pronounced dampening effect is obtained. On the other hand, the flow of liquid through a small lumen cannula fitted onto the cannula connector of the syringe is steadied.

In a further advantageous embodiment a greater resistance to pushing is obtained by means of suitable dimensioning of the plunger on the side inserted into the syringe barrel, by sealing means fitted onto the plunger, for example a circular sealing lip, or other suitable means. This has on the one hand to allow a large degree of smooth pushing of the plunger into the syringe barrel, but on the other hand it must be ensured by means of this flow resistance that even when released, particularly with complete release by the fingers, the plunger retains its depth of insertion and is not pushed backwards in the syringe barrel by the compressed air in the measuring channel and buffer. The use of such a syringe avoids excessively rapid slowing down of the flow of liquid through the cannula. In an advantageous further development, the resistance to pushing can also be dimensioned such that a certain tolerance in the depth of insertion of the plunger is allowed when the pressure is released.

The dampening property of a syringe according to the invention, important for a slow and even or steadied injection, is provided by means of a relatively high flow resistance, for example a small lumen cannula, counter to which the liquid is injected, and by means of a comparatively low flow resistance at least of a part of the measuring channel. The rear end of the measuring channel advantageously leads into the buffer of the plunger. A flow reducing means placed on the cannula connector of the syringe barrel which produces the necessary relatively high flow resistance also allows the use of a syringe according to the invention with large lumen cannulas which have a relatively large internal diameter and consequently a flow resistance which is too low for perfect operation of the syringe.

During the injection of a liquid, the pressure with which the liquid is injected results, in the case of a syringe, from at least two partial pressures, variable in their individual amounts at different times, but in sum almost invariable: By pushing the plunger into the syringe barrel, the pressure of the fingers is exerted directly upon the liquid located in the syringe barrel. On the other hand, too large a direct pressure, for example when the plunger is depressed suddenly, leads to ingress of the liquid into the measuring channel and compression of the air located in the measuring channel and in the buffer of the plunger. In this way, a pressure builds up here which can only be effective once the pressure of the fingers exerted on the plunger for injecting the liquid is eased, and to this extent is described as indirect pressure. If the plunger is pushed very rapidly into the syringe barrel, the injection of the liquid is done at this time largely as a result of a direct pressure; however if the fingers completely release the plunger, the liquid located in the syringe barrel is injected by means of indirect pressure—by decompression of the compressed air present in the measuring channel and buffer of the plunger.

In an advantageous embodiment of the invention, the pressure currently acting upon the liquid can be observed or measured in the measuring channel (liquid running further inside the measuring channel=increasing pressure; liquid dropping=reducing pressure). By means of a scale calibrated for a certain flow resistance, for example of a small lumen cannula, for example applied on or over the measuring channel, the pressure from the position of the boundary layer between liquid and compressible medium (meniscus) is given as the absolute value or directly as the speed of the injection, by determining the different resulting injection speeds when a certain cannula is used and with certain liquid levels in the measuring channel.

Good legibility of such a scale is obtainable by means of a very transparent substance, in particular plastics. As with a measuring channel arranged centrally in the buffer, the liquid level, in the case of a clear liquid, has to be recognised through a total of three layers of plastics, it is advantageous to arrange the measuring channel eccentrically in the buffer, that is to place it on the wall of the plunger. It follows that the liquid level in the measuring channel can mainly be seen well from one direction and can be reliably observed. If an oval cross-section is selected for the measuring channel, the liquid level observed from the wider side of the measuring channel is better recognisable under certain conditions, for example with suitable light refraction through the oval shape acting as a magnifying glass, without the volume of the measuring channel needing to be increased thereby.

An advantageous solution is to integrate the measuring channel in the wall of the plunger or to place it externally in a groove in the plunger so that in this case the liquid level in the measuring channel only has to be observed through two layers of plastics. A further advantage of this solution is that faulty readings of the liquid level, caused by parallax, on a scale fitted from the exterior onto the plunger are minimised. This is simple in production technology terms, and cheap to manufacture.

A further advantageous embodiment of the invention additionally provides an elongate recess in the syringe barrel. In this case the liquid level can be seen even better through only one layer of plastics.

In addition to a line scale, differently coloured ring or bar markings (for example green=correct injection speed, yellow=still acceptable injection speed, red=injection speed too fast) or different cross-sections of the measuring channel marking certain injection speed areas can be envisaged.

The retention of a certain, for example maximum permissible, injection speed can be defined in that the liquid level in the measuring channel must not exceed a certain mark, or the liquid may completely fill the measuring channel but not drip out of the measuring channel. Using this simple rule, correct injection, that is to say not too rapid, can easily be tested afterwards: Dripping of the liquid into the buffer shows faulty injection.

Measurement of the parameters previously described and of further parameters is also possible by using other, for example, inductive, opto-electrical or piezo-electrical measuring means. The parameters can then be adjusted, monitored, controlled or regulated according to which conditions have to be met by means of the invention.

Because of the decreasing changes in the liquid level in the measuring channel due to the increasing compression of the air in the measuring channel and buffer, step-wise increase in the pressure exerted on the plunger, each time by the same amount, has the following effect: When there is a small volume in the buffer and a relatively large volume in the measuring channel, a relatively large pressure area can consequently be determined over a relatively short scale; with this, the pressure changes are indicated sensitively when there is still low compression of the air in the measuring channel and buffer, and less sensitively with increasing pressure. However, with a relatively large volume in the buffer and configuration of the measuring channel as a long capillary, even small changes in pressure can be determined very sensitively, as they cause a clear change in the liquid level in the measuring channel.

Effective dampening of sudden, direct increases in pressure produced by the fingers on the plunger and a steadied flow of the liquid through a small lumen cannula with an injection speed increasing only slowly when the fingers release the plunger for a short time requires, in the case of a syringe according to the invention, a relatively small flow resistance to a part of the measuring channel, for example the front, first measuring channel aperture, compared to the flow resistance of the cannula placed on the cannula connector of the syringe barrel, and a relatively large dampening volume in the measuring channel and/or buffer. In order to have reliable control over the injection speed, changes in the pressure acting upon the liquid must always produce a sufficiently clear, that is to say easily recognisable, change in the liquid level in the measuring channel.

The ratio of the volume in the measuring channel to that in the buffer has an influence on the dampening behaviour of a device according to the invention, in particular a syringe. When there is a relatively large volume in the buffer the air is less highly compressed when there is a certain increase in the volume of liquid in the measuring channel than when there is a small volume in the buffer. When a large, weakly compressed volume of air is decompressed, there follows a slow and, in itself, very even pushing back of the liquid out of the measuring channel; when a large, highly compressed volume of air is decompressed, however, there is in particular initially a more rapid and then clearly slowing pushing back of the liquid out of the measuring channel. The dampening volume consequently also has the function of a buffer.

In a further development of the syringe according to the invention, the volume of air in the buffer of the plunger can be varied certain steps by means of different sealing pieces, or by means of a sealing piece moveable inside the plunger, continuously within certain bounds.

In this way, the dampening behaviour of the syringe can be altered in a simple manner, that is to say the syringe can be adjusted to be "harder" or "softer". With the same liquid level in the measuring channel, the injection speed can be altered with the same flow resistance, for example of a certain cannula. The possibility of setting a constant injection speed when there are different flow resistances, for example through different cannulas, is also of interest. This minimises the production costs: On the one hand a scale, for example on or over the measuring channel giving details of the injection speed, remains valid; on the other hand by using different sealing pieces, inexpensive syringes or syringe plungers with a wide range of buffer volumes, for example for different cannulas, are produced.

If the rear, second aperture of the measuring channel is sealed with a suitable sealing piece, that is to say the join between the measuring channel and the buffer of the plunger, the plunger then dampens using only the small volume of air located in the measuring channel, consequently "very hard", and measures the pressure correspondingly less sensitively. With a very small volume of air in the measuring channel the syringe behaves almost in the manner of a conventional syringe. If the volume of air in the measuring channel is somewhat larger, on the other hand, such a syringe makes it possible to work with two different dampening and pressure measuring areas which can be selected by displacing a suitable sealing piece in the plunger, without having to make an additional syringe barrel.

In accordance with the invention, a larger, in particular a substantially larger pneumatic damper can be integrated into the plunger of a syringe without the length of the syringe have to be altered in comparison to a conventional one.

When known syringes are sterilised, components can be damaged, particularly through repeated heat sterilisation; the use of metal parts makes sterilisation with gamma rays difficult. In particular, internal air spaces largely or completely sealed by means of appropriate seals are problematic in certain sterilising methods (heat, ethyl oxide). However, a syringe according to the invention—even when limited by the plastics used—can in principle be subjected to all sterilising methods. It is advantageous for this that this volume of air located in the plunger is only closed off when the liquid is drawn up into the syringe barrel.

As the air located in the measuring channel and the buffer of the plunger has inevitably to be sterilised when the syringe is sterilised, the direct contact of the liquid with this air presents no hygiene problems. Compared to a makeshift solution in which non-sterile atmospheric air is used, a syringe provides the greatest possible degree of safety for the patient in this respect also.

A syringe according to the invention permits ergonomic working, for example in a manner which is normal for the anaesthetist and in this way safe in its use on the patient. Compared to a more unwieldy and difficult makeshift solution, this ensures that during the period of injection, the correct depth position of the spinal needle is not lost during spinal anaesthesia.

The syringe according to the invention essentially requires no precision parts. The plunger can be produced as a simple injection moulded plastics part. The solution which is most simple in terms of production technology and is the most flexible in its application, is to produce the plunger of a syringe, up as far as the front, first join with the measuring channel, as a cylinder closed on one side and to seal this rear, open side with a suitable sealing piece, for example made from rubber or plastics, so that an internal hollow space is created as a buffer.

A circular sealing lip, for example made from rubber, fitted in the plunger also produces a sufficiently even resistance to pushing, even in a syringe barrel with a diameter which is not exactly to size, and prevents jolting movements of the plunger when pushed in. A simple and inexpensive solution is to directly injection mould such a circular sealing lip when producing the plunger, as is normal with the plungers of so-called low-cost single-use syringes. Good dampening of the possible abrupt movements of such a plunger when depressed into the syringe barrel require, however, a sufficiently large provision of dampening volume in the measuring channel and buffer.

A syringe according to the invention can be produced on high capacity machines. The problem of precision reproducibility of the volume of air enclosed between the two plungers of a syringe with plunger pressure dampening does not occur, as the volume of air in the measuring channel and buffer of the plunger varies only minimally and not to any relevant degree in the area of the precision of production of the parts required, for example, for the plunger, in particular when produced from plastics.

This syringe not only makes possible a slow and steadied injection of a local anaesthetic during spinal anaesthesia, but can also be used for pressure controlled injection of other liquids, for example when "blocking" a trans-urethral catheter. With this a balloon on the end of the tip of the catheter lying in the bladder is filled with liquid ("physiological" salt solution). If now an unusually high increase in pressure occurs while the catheter is being "blocked", which can be easily observed by means of the syringe, this indicates faulty positioning of the catheter. In this way, faulty positioning of the catheter which would otherwise be noticed too late can be recognised early, particularly in the case of sedated patients, and in this way injuries to the urethra can be prevented.

An advantageous embodiment of a syringe according to the invention is also suitable for exclusively measuring and control of pressure, for example of a liquid. For this, the syringe barrel as well as the cannula connector of the syringe are firstly vented and it is ensured that the plunger cannot slide back inside the syringe barrel during the measurement, for example by means of a restrictive circular sealing lip. This is pushed into the measuring channel by the pressure to be measured being applied to the liquid. A relative or, because of calibration, an absolute pressure value can be read from the level of liquid in the measuring channel.

By means of a further development, a syringe according to the invention can also be used only for pressure-controlled injection of a gas and as a simple, compact and sufficiently precise and inexpensive gas pressure measuring instrument compared to conventional manometers, for example in order to inflate a "cuff" (a balloon with which an endo-tracheal tube placed in the airway is sealed against the wall of the airway) with a certain pressure and then to monitor this pressure. For this, a separating means is inserted in the front, first aperture of the measuring channel of a syringe, such that it is sealed against the wall of the measuring channel in an air-tight manner, but can easily be pushed into it, for example an elastic stopper, for example made from rubber, or a drop of oil, which separates the air drawn into the syringe for inflating the "cuff" from the air located in the measuring channel and in the buffer of the plunger. If the air located in the syringe barrel is now compressed, the separating means in the measuring channel is pushed backwards and in this way the air located in the measuring channel and buffer of the plunger is compressed. From the position of the separating means with respect to a scale applied to the measuring channel—the separating means consequently also acts as an indicator—the pressure can be read off either as a relative value, or after calibration, as an absolute value. By changing the volume of air in the buffer of the plunger, the pressure indication range can also be finely adjusted with this syringe also, or, by sealing the rear, second aperture of the measuring channel with a suitable sealing piece, can be changed significantly.

In accordance with the principle of a dampening and pressure measuring means integrated into the plunger, further applications are possible: By using a barrel without an outlet aperture, dampening elements, for example a small volume of air in the buffer of the plunger, or a relatively large volume of air in the measuring channel, or pressure measuring instruments, for example a large volume of air in the buffer, or a small volume of air in a long and thin measuring channel, can be used.

Possibilities for use of the invention will be described hereinafter. The representation of the invention in the medical field does not restrict the use of a method according to the invention and a device according to the invention in other fields of application.

a. Spinal anaesthesia: A pressure controlled and consequently a speed controlled injection of local anaesthetic reduces the danger of nerve damage by the injection stream.

An even, in particular steadied injection of hyperbaric or hypobaric local anaesthetic allows one-sided spinal anaesthesia.

An even or evened out injection of hyperbaric local anaesthetic allows improved control of bilateral spinal anaesthesia, for example "saddle block" anaesthesia.

b. Slow and even injection of a fluid, for example a medicine which because of its effects on the circulation or a powerful vascular irritant effect cannot be injected quickly; for example propofol=an intravenous narcotic; a microprocessor controlled pump for the correct, that is to say not too rapid, inject ion of the narcotic dose, can be omitted.

c. Pressure-controlled injection of ultrasound contrast media ("micro-bubble " solutions): When the injection pressure is too great, the small gas bubbles are destroyed.

d. Use as a dosing device, in particular a micro-dosing device, for example for injection of small amounts of a fluid, for example in the medical field, of a medicine with a powerful effect on the circulation, "pre-filling" of the infusion in centravenous catheters; the volume of liquid to be injected is injected (up) into the correspondingly large or small volume measuring channel, initially with the outlet aperture of the syringe barrel closed, for example by means of a three-way tap. After opening of the outlet aperture of the syringe barrel, exactly the amount located in the measuring channel is then quickly injected ("bolus") with low injection resistance, or when there is a large injection resistance, for example because of a flow reduction piece, slowly injected.

e. The syringe is used as a "pressure sensor", for example in peridural anaesthesia: the syringe (measuring channel open at the rear=large volume of air=low-pressure variant) is pressurised counter to the comparatively high intra-ligament injection resistance, by depressing the plunger. Once the peridural space is reached, the column of liquid in the measuring channel of the syringe drops abruptly because of the sudden easing of the injection resistance.

This technique permits two-handed, controlled insertion of the peridural needle compared to the classical loss-of-resistance technique, and delivers a clear optical signal once the peridural space is reached.

Conventional loss-of-resistance syringes can also be equipped with a simple pressure measuring means in the plunger (measuring channel closed at the rear=small volume of air=high-pressure variant).

The advantages of the two loss-of-resistance techniques—with air and liquid or another fluid—can be advantageously combined thus: On the one hand the "feeling" and the "observation" of the spring plunger according to the "air" technique, as long as the tip of the peridural needle is in the intraligament position, and the loss of springiness when the peridural space is reached. On the other hand, the spring actuation according to the "liquid" technique resulting from the increasing rise in pressure when the plunger is further depressed, and consequently "direct feeling" of the suddenly easing injection resistance once the peridural space is reached. By combining the two loss-of-resistance techniques, changes in the injection resistance can be evaluated not only subjectively (by "feeling" the loss of resistance) but also objectively by the anaesthetist carrying out the procedure and by any observer (pressure measurement).

In addition, the injection of non-sterile air into the peridural space is avoided.

f. Pressure-controlled "blocking", for example with liquid, of balloon catheters, for example bladder catheters or embolectomy catheters (Fogarty): By measuring the pressure with which the balloon of the catheter is "blocked", faulty positioning or a perilous state of the balloon (with excessively high pressure increase) can be recognised and the danger of damage, for example injury to the urethra or a vessel, is reduced.

g. Pressure-controlled "blocking", for example with air, and continuous pressure control of a tubular cuff or pulmonary catheter (swan-neck) by means of a syringe with a separating means in the measuring channel.

h. Modification of perfusion syringes: When the syringe barrel is empty, and consequently the delivery end of the perfusion pump, the injection does not stop abruptly but ceases slowly by delivering the volume located in the measuring channel. With an appropriately long measuring channel, for example a wound tube, it is possible to have a substantial "buffer volume".

Perfusion syringes, in particular perfusion syringes with medicines with a powerful effect on the circulation (for example catecholamine therapy for intensive-care patients) can be replaced without risk even when there is only one perfusion pump.

Moreover, control of delivery is possible, as when there is a closure, for example a kinked infusion line, the liquid is pushed further into the measuring channel. An increase in pressure can be recognised more quickly, for example by means of a sensor (coil, photoelectric cell, line contact and so forth) than by means of the closure pressure alarm of the perfusion pump.

Further, the unintentional supply of a bolus, for example by excessively high supply pressure, can be avoided as the pressure correlating with the desired speed of supply can be adjusted or controlled precisely before the perfusion syringe is "switched on".

i. Pressure and/or delivery control of conventional perfusion syringes: In this case, a syringe according to the invention is connected parallel to the perfusion syringe as a "pressure measuring means" by means of a three-way tap.

j. Pressure control of pressure infusions or flush infusions, in the medical field for example during arterial or central venous pressure measurement: Using a syringe according to the invention (high-pressure variant, see e.) connected parallel to the infusion leg, the pressure created and maintained by a simple pressure cuff is measured directly in the infusion system and not indirectly via a conventional manometer, sometimes in need of repair, which shows the pressure in the pressure cuff.

k. Identification or location of cavities, for example bodily cavities: Pleural puncture for inserting a drain or a catheter, abdominal puncture for endoscopic procedures, tracheal puncture for bougie tracheostomy, or bladder puncture for insertion of a supra-pubic catheter. The syringe is inserted in the manner of a "pressure sensor" (see e.). The sudden injection of the volume of liquid located in the measuring channel of the syringe which occurs when the injection resistance is eased produces an injection stream which pushes the injured structures, for example the lung or intestine, away from the tip of the needle, and consequently reduces the danger of damage to these structures.

l. Measurement of a pressure or a pressure difference in the medical field, for example, of the central venous or arterial (average) pressure. Compared to the riser otherwise used for measuring the central venous (average) pressure in a centimetric water column, the syringe is a more manageable and compact pressure measuring means.

The measuring channel can be divided, by means of different cross-sections into a front, precise, low pressure measurement area (measurement of the central venous (average) pressure=long and small lumen measuring channel piece) and a rear high pressure measurement area with other measurement tolerances (measurement of the arterial (average) pressure=short and large lumen measuring channel piece).

Measurement of negative pressure is also possible, that is to say low pressures: After drawing up the liquid into the syringe barrel, the plunger is opened counter to the atmospheric pressure, for example by means of a slider or two apertures rotatable with respect to one another in the plunger and the sealing piece. After the outlet aperture of the syringe barrel is closed, by depressing the plunger some liquid has been forced into the measuring channel, for example up to a zero mark, for example of half of the measuring channel, the plunger is again sealed against atmospheric pressure in an air-tight manner. Both positive and negative pressures can now be measured.

In contrast to the tube line which is always open to the atmospheric pressure, the syringe is a closed system; this has hygienic advantages.

m. Punctures of liquid spaces, in the medical field for example blood vessels, bladder for insertion of a supra-pubic bladder catheter, puncture of a pleural contusion, ascites puncture; a syringe prepared for measurement of negative pressure (see l.) is fitted in an air-tight manner to the puncture cannula. After insertion of the puncture cannula the plunger is pulled back in the syringe barrel until the low pressure desired is established. With appropriate configuration of the circular sealing lip of the plunger, the plunger is retained in its position in the syringe barrel and consequently the low pressure set is maintained. When the tip of the puncture cannula reaches the liquid space, the liquid level in the measuring channel increases abruptly, until a maximum of pressure equalisation.

Such a pressure-controlled aspiration (=suction) can prevent elastic or yielding walls of other elastic walls being suctioned during puncture, which is otherwise possible using strong aspiration, in the medical field for example when a blood vessel is punctured, the vessel wall can be suctioned onto the cannula aperture. As in such a case no blood is to be aspirated, it is falsely assumed that the blood vessel has not yet been reached or has already been passed. In this way the number of faulty of multiple punctures is increased.

In addition, pressure measurement in the punctured vessel is possible. When attempting to puncture a central vein, unintentional puncture of an artery can be directly recognised. After the puncture, by means of injection of liquid, for example saline solution, the puncture cannula can be flushed directly; blockage of the cannula by flowing blood is prevented in this way.

BRIEF DESCRIPTION OF THE DRAWINGS

Further advantages and characteristics of the invention will be explained with reference to the preferred embodiments shown in the drawings. These show, in.

DETAILED DESCRIPTION OF THE INVENTION

Figure 1:
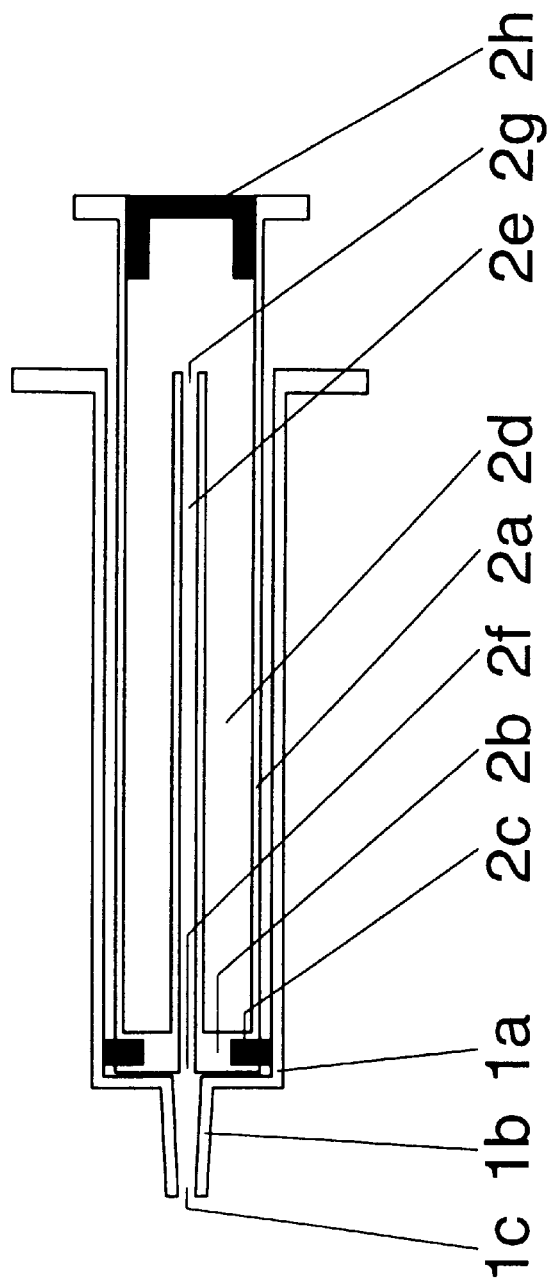
FIG. 1 a syringe with a buffer integrated into its plunger and a measuring channel for steadied and pressure-controlled injection of a fluid, for example, a liquid or a gas, seen through the centre, FIG. 2 a syringe according to FIG. 1 with a large lumen cannula attached, seen through the centre, while a fluid is being drawn up through the large lumen cannula into the syringe barrel, FIG. 3 a syringe according to FIG. 1 with a small lumen cannula attached, seen through the centre, while a fluid located in the syringe barrel is being injected through the small lumen cannula, FIG. 4 a syringe according to FIG. 3 with a flow reduction piece connected and a large lumen cannula attached (shown in broken lines), seen through the centre, while a fluid located in the syringe barrel is being injected through the flow reduction piece, FIG. 5 a syringe according to FIG. 3, seen through the centre, with a sealing piece which can be pushed inside the plunger and does not seal the rear aperture of the measuring channel, FIG. 6 a syringe according to FIG. 5, seen through the centre, with a sealing piece pushed into the plunger, and sealing the rear, second aperture of the measuring channel, FIG. 7 a syringe according to FIG. 1, seen through the centre, with a separating means tightly sealing the front, first aperture of the measuring channel, and which can be pushed easily in the measuring channel, FIG. 8 a syringe according to FIG. 3 with a tube line connected, seen through the centre, while a fluid, for example air, located in the syringe barrel is being injected into a tube line, FIG. 9 a diagram showing the flow rate over the pressure, dependent upon the thin spinal needle used as the flow resistance, FIG. 10 a diagram showing the resulting pressure over the compression of a compressible medium in buffers of different sizes of a plunger of a device according to the invention.

FIG. 1 shows an advantageous embodiment of the invention in the form of a syringe with an internally hollow plunger 2a lying inside the syringe barrel 1a, sealed with respect to the inside wall of the syringe barrel 1a on the side pushed inside the syringe barrel 1a by means of a circular sealing lip 2c lying inside the barrel 2b of the plunger 2a, and closed on the side projecting outside the syringe barrel 1a, with a sealing piece 2h. The syringe barrel 1a and the base of the plunger 2a together form a container of variable volume, that is to say dependent upon the setting of the plunger 2a. From the centre of the barrel 2b there leads into the buffer 2d of the plunger 2a, via a front, first aperture 2f and a rear, second aperture 2g, a measuring channel 2e open on both sides. The buffer 2d and the measuring channel 2e are filled with a compressible medium, in this case air.

Figure 2:
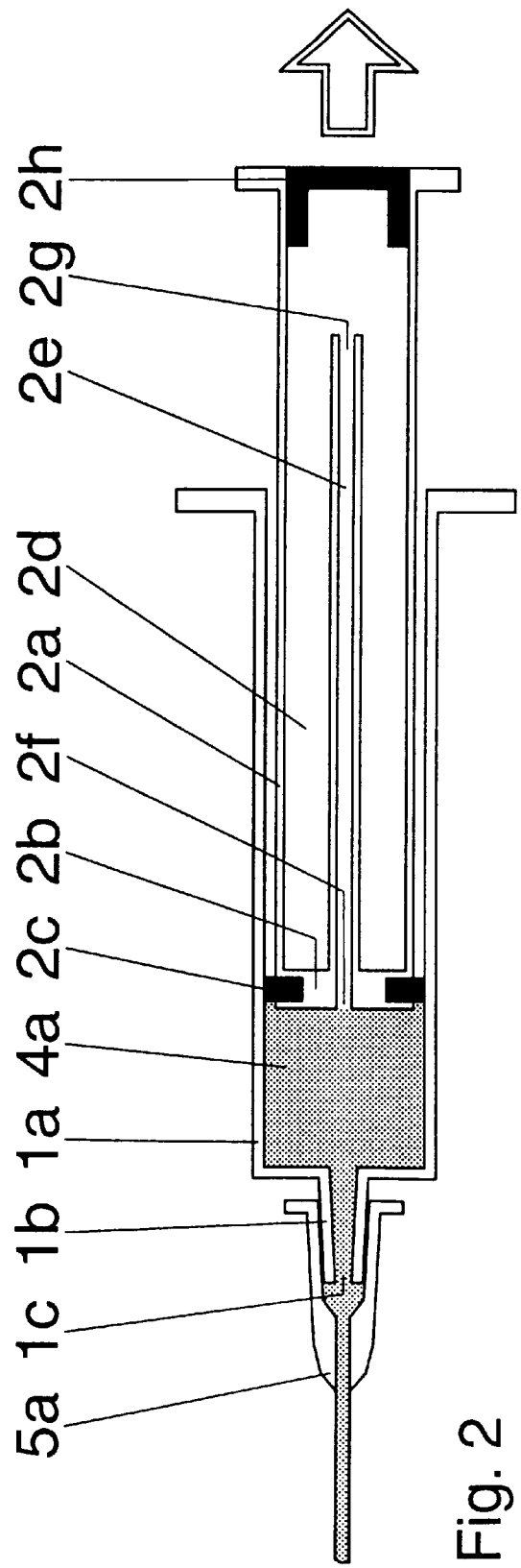

FIG. 2 shows large lumen cannula 5a attached to the cannula connector 1b of the syringe barrel 1a, which has an internal diameter comparable to that of the outlet 1c of the syringe barrel 1a, and consequently has a relatively low flow resistance. This is helpful for the drawing up of a liquid 4a, for example a medicine. By pulling back the plunger, indicated by the arrow, the liquid 4a is drawn into the syringe barrel 1a, in this way the liquid 4a moves into the front, first aperture 2f of the measuring channel 2e, lying centrally in the barrel 2b of the plunger and seals off the compressible medium located in the measuring channel 2e and the buffer 2d of the plunger 2a from the outside.

FIG. 3 shows a small lumen cannula 5b attached to the cannula connector 1b of the syringe barrel 1a, shown reduced in length, which has a small internal diameter and consequently a relatively high flow resistance. Because of a clearly lower flow resistance of the front, first aperture 2f of the measuring channel 2e, by now pushing in the plunger 2a, indicated by the arrow, when a certain pressure acting upon the liquid 4a is exceeded, liquid 4a is pressed into the measuring channel 2e, the compressible medium is displaced out of the measuring channel 2e into the buffer 2d of the plunger 2a and in this way the compressible medium is compressed. If now, the pressure acting upon the liquid 4a by depressing the plunger 2a is relieved, the liquid 4a is pushed out of the measuring channel 2e again by the compressed compressible medium due to decompression. The circular sealing lip 2c lying in the barrel 2b is dimensioned such that jolt-free pushing of the plunger 2a into the syringe barrel 1a is possible and the plunger 2a retains its depth position in the syringe barrel 1a even when the finger pressing on the plunger 2a is released completely. In this way, on the one hand pressure increases because of too rapid pushing of the plunger 2a into the syringe barrel 1a are dampened, and on the other hand the flow of the liquid 4a through a small lumen cannula 5b is evened out. FIG. 3 also shows the use of the syringe for locating a cavity 10 in a body 9. For this, the cannula 5b is slowly inserted into the body 9, while at the same time the fluid 4a is kept under a certain pressure. When the tip of the cannula 5b reaches the cavity 10, the fluid 4a can suddenly leave the cannula 5b more easily, which results in a drop in pressure in the syringe barrel 1a, which can easily be recognised by a sudden lowering of the boundary layer 8 in the measuring channel 2e. When using a large lumen cannula 5b, the drop in pressure, with otherwise the same conditions, can be seen more clearly than with a small lumen cannula 5b.

FIG. 4 shows a situation corresponding to FIG. 3, wherein a flow reduction piece 6 is connected to the cannula connector 1b of the syringe barrel 1a, which provides a relatively high flow resistance important for a for a slow and evened out injection of the liquid 4a. When using a flow resistance piece 6 injection can be done slowly and evenly also with a large lumen cannula 5a despite its small flow resistance.

FIG. 5 shows a situation corresponding to FIG. 3, wherein the volume of the compressible medium in the measuring channel 2e and buffer 2d of the plunger 2a has been reduced by a larger sealing piece 2i. By altering the volume of compressible medium located in the measuring channel 2e and buffer 2d, the dampening properties of the syringe can be altered. In this way the syringe can be adjusted to differently sized flow resistances of different cannulas, so that a certain liquid level in the measuring channel 2e always corresponds to a certain injection speed.

FIG. 6 shows a situation corresponding to FIG. 5, wherein the rear, second aperture 2g of the measuring channel 2e has been closed by pushing the sealing piece 2i into the plunger 2a. By means of this considerable reduction of the volume of compressible medium located in the measuring channel 2e, the dampening behaviour of the syringe is considerably altered. In this way the syringe can be used in two different dampening and pressure measurement areas.

FIG. 7 shows a situation comparable to FIG. 1, wherein by means of a separating means 3, for example an elastic stopper or a drop of oil, which closes the front, first aperture 2f of the measuring channel 2e, in particular in an air-tight manner, yet nevertheless can be easily pushed into the measuring channel 2e, and the compressible medium located in the measuring channel 2e and buffer 2d is closed to the outside. A gas 4b, for example air, can also be injected in a pressure-controlled manner using a syringe modified in this way.

FIG. 8 shows a situation comparable to FIG. 3, wherein instead of a liquid 4a, which can also be injected using such a syringe, a gas 4b, for example air, is injected into a tube line 7. The position of the separating means 3, for example an elastic stopper, a drop of oil and so forth, in the measuring channel 2e shows the pressure acting upon the gas 4b during the injection, indicated by the arrow. The pressure measurement can take place as relative pressure measurement or with calibration of the device as absolute value measurement. The sealing piece 2j is dimensioned so that the separating means 3 cannot or can only with difficulty be pushed out of the measuring channel 2e.

Figure 9:
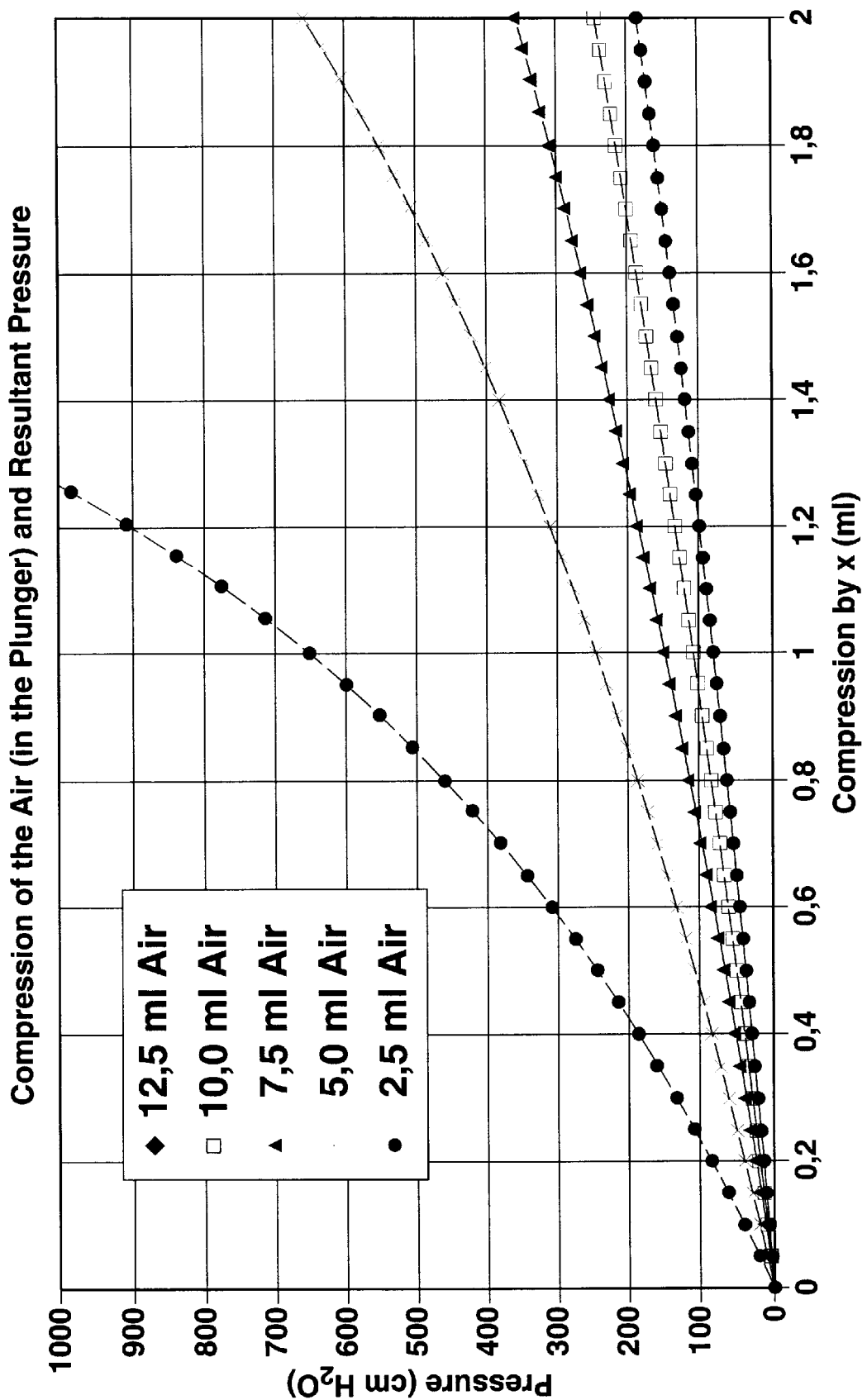

FIG. 9 shows a diagram of the flow rate over pressure dependent upon thin spinal needles used as flow resistance. It shows that a regular, low rate of flow is achieved only with difficulty as even with small changes in pressure the flow rate differs significantly. In particular when conventional syringes are used, such pressure changes occur in an uncontrollable and undampened manner with freehand injections.

Figure 10:
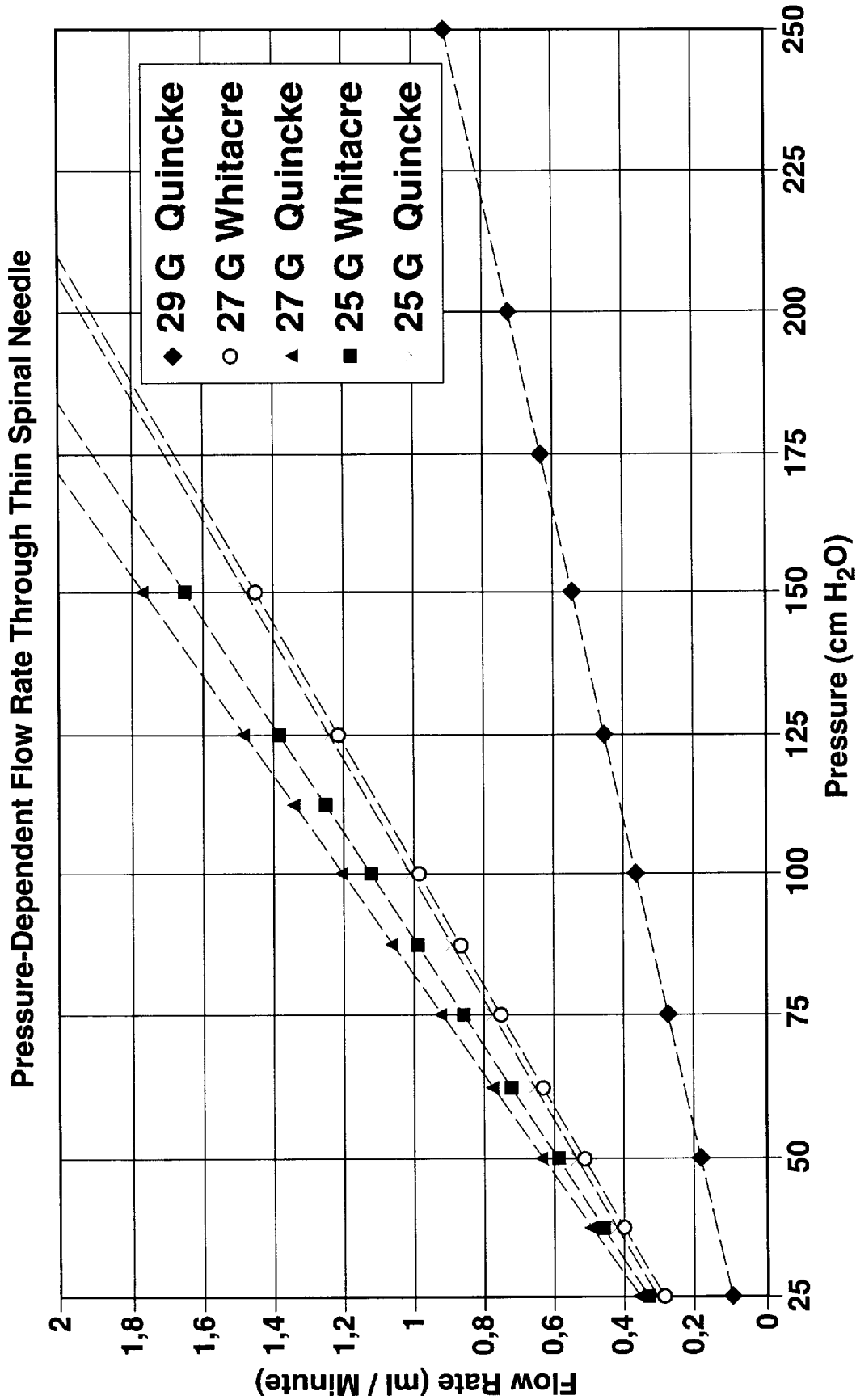

FIG. 10 is a diagram showing the resulting pressure over compression of a compressible medium, in this case air, in a buffer of a plunger of a device according to the invention. It makes clear the dampening properties of different volumes of compressible medium in a device according to the invention. Thus in accordance with the desired dampening and the evening out of the flow rate resulting from this, an appropriate buffer volume can be established in the device, for example by altering the buffer in the plunger of the syringe.

The present invention permits a simple visual or measurement check of the pressure when handling a fluid, whereby in particular medical procedures, such as the injection of a fluid, can be substantially facilitated and improved.

List of Designations 1a container, syringe barrel
1b cannula connector
1c outlet, outlet aperture
2a pressure production means, plunger
2b plunger cylinder
2c sealing means, circular sealing lip, friction means
2d buffer
2e measuring channel
2f front, first aperture
2g rear, second aperture
2h, 2i, 2j different sealing pieces
2k measuring means, scale
3 separating means (elastic stopper, drop of oil)
4a, 4b fluid (liquid, gas)
5a, 5b different cannulas
6 flow reduction piece
7 tube line
8 boundary layer between the fluid and compressible medium
9 body
10 cavity

What is claimed is:

1. A method for pressure-controllable handling of a fluid comprising the steps of:
    forcing the fluid located in a container of a variable volume through an outlet by applying pressure with a plunger upon the fluid wherein
        the container is connected to a measuring channel with a pre-determined cross-section,
        the measuring channel communicates with a buffer with a pre-determined constant volume,
        the measuring channel and the buffer are filled with a compressible medium, such that there is at least partial ingress of the fluid into the measuring channel, dependent upon the influence of pressure, the cross-section of the measuring channel and the size of the buffer volume,
        the measuring channel is provided with a measuring means for observing the pressure of the fluid,
        the buffer is in the plunger, and
        the measuring channel is in the buffer or the plunger.

2. The method of claim 1 wherein the volume of the buffer is at least 10 times as large as the volume of the measuring channel.

3. The method of claim 1 wherein the volume of the buffer is at least 100 times as large as the volume of the measuring channel.

4. The method of claim 1 wherein the application of pressure is pressure-controllable.

5. The method of claim 1 wherein the application of pressure comprises pushing a plunger which can be pushed into the container, which is guided in a sealed manner along the interior walls of the container.

6. The method of claim 1 further comprising the step of observing and measuring the position of a boundary layer between the fluid and the compressible medium in the measuring channel during the application of pressure upon the fluid.

7. The method of claim 6 further comprising the steps of producing a certain pressure in the container, moving a cannula connected to the outlet into a body and locating and identifying an area in the body which has a pressure different from the certain pressure produced in which a change of position of the boundary layer is observed.

8. The method of claim 6 further comprising the step of adjusting the pressure acting upon the fluid dependent upon the position of the boundary layer.

9. A device for pressure-controllable handling of a fluid comprising:
    a container of variable volume for receiving the fluid,
    a pressure producing means for producing a pressure acting upon the fluid,
    an outlet for the entrance and/or exit of the fluid,
    a measuring channel with a pre-determined cross-section, which is connected to the container,
    a buffer with a pre-determined constant volume, which communicates with the measuring channel,
    wherein the measuring channel and the buffer are filled with a compressible medium, and
    wherein the measuring channel is provided with a measuring means for observing the pressure of the fluid, and wherein the buffer is in the pressure producing means and the measuring channel is in the buffer or the plunger.

10. A device for pressure-controllable handling of a fluid comprising:

a container of variable volume for receiving the fluid, a plunger for producing a pressure acting upon the fluid, an outlet for the entrance and/or exit of the fluid, a measuring channel with a pre-determined cross-section, which is connected to the container, a buffer with a pre-determined constant volume, which communicates with the measuring channel, wherein the measuring channel and the buffer are filled with a compressible medium, and wherein the measuring channel is provided with a measuring means for observing the pressure of the fluid, and wherein the buffer is in the plunger and the measuring channel is in the buffer or the plunger.

11. The device of claim 10 wherein the volume of the buffer is at least 10 times as large as the volume of the measuring channel.

12. The device of claim 10 wherein the volume of the buffer is at least 100 times as large as the volume of the measuring channel.

13. The device of claim 10 wherein the pressure producing means is a plunger which can be pushed inside the container, which is sealed with respect to the internal wall of the container.

14. The device of claim 10 wherein the measuring channel is arranged in the plunger and leads into a first aperture in the space for the fluid formed by the container and the plunger.

15. The device of claim 10 wherein the measuring channel leads into a second aperture in a buffer.

16. The device of claim 10 wherein the buffer is arranged inside the plunger.

17. The device of claim 10 wherein walls of the container, walls of the plunger and walls of the measuring channel are transparent and one of these walls, is provided with a scale for determining the position of a boundary layer between the fluid and the compressible medium in the measuring channel.

18. The device of claim 10 wherein the compressible medium and the fluid located in the container are separated from one another by a separating means which does not mix with the fluid and the compressible medium.

19. The device according to claim 10 wherein the compressible medium is air.

20. The device of claim 18 wherein the separating means can be pushed into the measuring channel in a sealing manner, but with negligible resistance compared to the forces naturally occurring.

21. The device of claim 10 wherein the buffer is arranged in the interior of the plunger and the measuring channel centrically in the interior of the buffer.

22. The device of claim 10 wherein the measuring channel lies eccentrically in the plunger.

23. The device of claim 10 wherein the measuring channel lies close to an outer wall of the plunger.

24. The device of claim 10 wherein the size of the volume of the buffer can be altered.

25. The device according to claim 10 the size of the volume of the buffer can be altered.

26. The device according to claim 10 wherein the volume of compressible medium located in the buffer of the plunger can be determined by a sealing piece arranged in the plunger.

27. The device of claim 10 wherein the size of the volume of the buffer can be altered, the volume of compressible medium located in the buffer of the plunger can be determined by a sealing piece arranged in the plunger, and the sealing piece is movable for adjusting the volume of the buffer.

28. The device of claim 10, wherein the compressible medium located in the measuring channel can be separated by means of a sealing piece from the compressible medium which is located in the buffer of the plunger.

29. The device of claim 10 wherein the buffer is provided with the sealable connecting aperture to the surrounding atmosphere.

30. The device of claim 10 wherein the compressible medium is a gas.

31. The device of claim 10 wherein the device is substantially cylindrical.

32. The device of claim 10 wherein the device is a syringe.

33. The device of claim 13 wherein friction means are present which hold the plunger in any position relative to the container set by force applied from the outside, even when this force is removed.

34. The device of claim 10 wherein the outlet or a cannula placed on a cannula fitting or a flow reduction piece has a smaller outlet cross-section than the cross-section of the measuring channel.

35. The device of claim 10 wherein the cross-section of the outlet, the cross-section of the measuring channel and the volume of the buffer are dimensioned according to each particular application and the pressures required for it, such that there is at least partial ingress of the fluid into the measuring channel during handling.

36. The device of claim 10 wherein the measuring channel is formed within the outer wall of the plunger.

37. The device of claim 10 wherein a flow reduction piece has a smaller outlet cross-section than the cross-section of the measuring channel.

38. The device of claim 10 wherein the pressure producing means is a plunger which can be pushed inside the container, which is sealed with respect to the internal wall of the container by sealing means.

39. The device of claim 10 wherein the plunger is provided with a measuring means for measuring the pressure of the fluid.

* * * * *